United States Patent
Frost et al.

(10) Patent No.: US 6,701,771 B2
(45) Date of Patent: Mar. 9, 2004

(54) MULTI-FRICTION SLEEVE PENETROMETER APPARATUS AND METHOD

(75) Inventors: James David Frost, Atlanta, GA (US); Jason Theodore DeJong, Davis, CA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 09/907,412

(22) Filed: Jul. 17, 2001

(65) Prior Publication Data

US 2002/0026824 A1 Mar. 7, 2002

Related U.S. Application Data

(60) Provisional application No. 60/218,817, filed on Jul. 18, 2000.

(51) Int. Cl.[7] .............................................. G01N 3/00
(52) U.S. Cl. ........................................... 73/9; 73/84
(58) Field of Search ................................ 73/9, 84, 784

(56) References Cited

U.S. PATENT DOCUMENTS

| 4,156,469 | A | | 5/1979 | Laskey | 175/58 |
|---|---|---|---|---|---|
| 4,382,384 | A | | 5/1983 | Mitchell et al. | 73/594 |
| 4,398,414 | A | * | 8/1983 | MacGregor | 73/84 |
| 4,492,111 | A | * | 1/1985 | Kirkland | 73/84 |
| 4,750,570 | A | | 6/1988 | Barrett | 175/4 |
| 5,319,959 | A | * | 6/1994 | Cooper et al. | 73/84 |
| 5,490,565 | A | * | 2/1996 | Baker | 166/379 |
| 5,886,253 | A | * | 3/1999 | Joustra | 73/84 |
| 6,062,090 | A | | 5/2000 | Bachhuber et al. | 73/784 |
| 6,208,940 | B1 | * | 3/2001 | Kram et al. | 73/84 |
| 6,254,769 | B1 | * | 7/2001 | Whittaker | 210/95 |

FOREIGN PATENT DOCUMENTS

| SU | 1392198 | * | 4/1988 | 73/84 |
|---|---|---|---|---|

* cited by examiner

Primary Examiner—Robert R Raevis (57) ABSTRACT

Disclosed are apparatus and method for determining interface strength in situ. In one embodiment, the apparatus includes a plurality of load cells, wherein each load cell obtains an in situ measurement of interface strength at each measurement depth that corresponds to location of each load cell on the attachment module. Each load cell obtains the in situ measurement of interface strength without using the measurement data of a penetrating tip member. In another embodiment, an apparatus for determining interface strength in situ comprises an attachment module coupled to a penetrating tip, wherein the attachment module includes a plurality of load cells. Each load cell includes a friction sleeve, which the friction sleeve of at least one load cell is configured with a different surface texture than another load cell.

29 Claims, 6 Drawing Sheets

MULTI-FRICTION SLEEVE PENETROMETER APPARATUS AND METHOD

This application claims priority to copending U.S. provisional application entitled, "Multi-Friction Sleeve Cone Penetrometer Attachment," having Ser. No. 60/218,817, filed Jul. 18, 2000, which is entirely incorporated herein by reference.

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of CMS-9978630 awarded by the National Science Foundation of the U.S.

CROSS-REFERENCE TO RELATED APPLICATION

TECHNICAL FIELD

The present invention is generally related to geotechnical systems and structure elements and, more particularly, is related to an apparatus and method for in situ measurement of the relationship between interface strength and surface roughness of civil engineering construction materials for the purpose of establishing friction parameters and characteristics.

BACKGROUND OF THE INVENTION

In geotechnical engineering, one of the most important factors for consideration when designing geotechnical systems is the particulate-continuum interface. This interface occurs between the soil and the geotechnical structural members (e.g. soil-concrete, soil-steel, soil-geomembrane). Although a significant amount of research has been performed on the behavior of soil masses under typical loading and straining conditions in geotechnical systems, the region where the geotechnical structural members and soil masses come into contact—the soil-geomaterial interface—has received markedly less attention.

The interface is the primary factor governing the performance of many geotechnical systems, including for example deep foundations, micro-tunneling, liner systems (e.g. landfills, canal liners, leach ponds), and an assortment of retaining structures such as anchored, reinforced, and soil nailed walls. The importance of the characteristics and behavior of the interface between man-made geomaterials and soils in the overall system performance varies from application to application, but is usually reflected in some manner in the design methodology and associated calculations for each geotechnical system. Because the structural integrity of many systems is dependant upon accurate calculations and designs for the soil-geomaterial interface, correctly measuring, calculating and designing the performance characteristics of the interface is crucial.

There are many different types of penetrating probes for detecting and measuring soil properties and characteristics or for detecting and measuring the properties and characteristics of underground substances, such as water, gases, contaminants, etc. Probes that test for underground substances are often used primarily in association with environmental applications. For instance, U.S. Pat. Nos. 6,208,940 and 6,236,941 both to Kram describe a piezocone having a conical tip attached to the lower end of a smooth friction sleeve, where the sleeve measures the resistance of the soil. The Kram inventions use the piezocone to develop hydrostatic and hydraulic plots for detecting the depth of subsurface water and groundwater contamination.

In U.S. Pat. No. 5,663,649 to Topp, a soil penetrometer and method are disclosed which are capable of determining the soil moisture content via in situ measurements and simplified calculations. The penetrometer has a releasably engageable tip and utilizes an electromagnetic field to detect moisture. Other prior art utilizes a variety of techniques in combination with penetrometers to detect and measure in situ characteristics, such as chemical composition for identification of contamination. For instance, U.S. Pat. No. 6,097,785 to Elam discloses the use of a penetrometer equipped with x-ray fluorescence spectroscopy to identify hazardous waste; U.S. Pat. No. 6,147,754 to Theriault uses laser induced breakdown spectroscopy in conjunction with a penetrometer to identify soil contamination; U.S. Pat. No. 6,018,389 to Kyle uses fiber optic raman spectroscopy probes to provide in situ chemical analysis; and U.S. Pat. No. 5,497,091 to Bratton teaches the use of cone penetration testing (CPT) in conjunction with a surface-mounted pH sensor to provide continuous pH profiling with depth during penetration.

It is also known in subsurface testing systems to utilize cone and sleeve strain sensors to detect certain soil characteristics. In U.S. Pat. No. 5,635,710 to Reed, a detachable sleeve is used to provide strength and protection to the radiation sensor probes which detect subsurface formations, and U.S. Pat. No. 5,902,939 to Ballard discloses a penetrometer having cone and sleeve strain sensors used to calculate soil classifications and soil layers in "real-time" during penetration. Likewise, in U.S. Pat. No. 5,726,349 to Palmertree, a system and method for determining the shear resistance of soil with a portable and partially automated cone penetrometer is provided, where the field data outputs are stored and then transferred to a computer for tabulating.

Clearly, the ability to accurately measure and anticipate the behavior of soil-geomaterial interfaces does not exist and development of such a system would lead to more accurate and reliable prediction of interface strength and more efficient geotechnical structure designs.

Thus, a heretofore unaddressed need exists in the industry to address the aforementioned deficiencies and inadequacies.

SUMMARY OF THE INVENTION

Briefly described, one embodiment of the system, among others, can be implemented as follows. A multi-friction sleeve penetrometer attachment apparatus that substantially eliminates the need for many of the empirical adjustment factors currently required in the estimation of interface strength. The attachment includes a plurality of individual load cells configured in series, each of which measures the interface resistance due to the penetration of a sleeve with a selected surface texture into the soil. This configuration provides for multiple individual in situ measurements of interface strength at each measurement depth in a single sounding. The sleeves are interchangeable so that measurements corresponding to any desired roughness can be determined. In addition, with multiple $f_s$ values recorded at any given elevation within the same sounding, factors that affect $f_s$ can easily be determined since the lateral variability of the site is not an issue in the measurements.

In a preferred embodiment, the attachment module is configured with four individual load cells, each having a mandrel and a friction sleeve. Thus, the four load cells correspond to four multi-friction sleeve module measurements of interface strength. Additionally, in a preferred embodiment, the attachment module is configured with a conventional 15 cm² CPT, allowing for simultaneous measurements of conventional CPT sensors (e.g. $q_c$, $u_2$, and $f_s$) in addition to the four multi-friction sleeve module measurements. Thus, the combined CPT module-attachment module system can provide seven individual in situ measurements of interface strength at each measurement depth in a single sounding.

In another embodiment, non-instrumented tips of varying lengths can be used with the penetrometer attachment in place of a conventional CPT module. Regardless of the specific configuration utilized, it is anticipated that the penetrometer attachment will enable direct in situ measurement of the relationship between surface roughness and hardness and interface strength.

These embodiments provide a method for determining in situ soil properties. In particular, a method is disclosed for direct, in situ measurement of the interface strength throughout the soil profile depth by determining the relationship between the interface strength and the hardness and surface roughness factors at desired measurement depths in a single sounding. In this regard, one embodiment of such a method, among others, can be broadly summarized by the following steps: collecting penetrating tip measurements; collecting attachment module measurements for each of said plurality of individual load cells, where said load cells are comprised of a corresponding plurality of friction sleeves; and transmitting said measurement data to a data acquisition system for manipulation and storage. This method may also include the steps of monitoring verticality, converting analog data to digital data, multiplexing data signals downhole, arranging a plurality of load cells in series, and configuring the attachment module for rapid set-up and easy modifications and configuring the friction sleeves with a diamond textured sleeve surface that is "self-cleaning" and capable of inducing shearing within the soil, instead of just along the interface.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

A multi-friction sleeve penetrometer attachment and method have been developed that allow for direct in situ measurement of interface strength. This device can eliminate the need for a number of critical empirical adjustment factors currently required in the estimation of interface strength.

Through recent advances in the study of particulate-continuum interfaces, two factors have been identified which are considered instrumental in identifying the behavior of the interfaces, namely the surface roughness and hardness. First, the continuum surface roughness should be quantified kinematically in a dimensionless manner in relation to the size of the contacting particulate media. This is accomplished by quantifying the effective roughness experienced by contacting particles. Second, the hardness of the surfaces must be quantified using established hardness tests. While each of these factors has been known for some time, the importance of their coupled effect on interface strength had not been uncovered.

In many cases, the behavior of the interface is currently estimated by applying a series of adjustment factors to estimated properties of the soil mass. In other cases, the soil-geomaterial interface strength is determined through interface shear tests performed in the laboratory and then corrected by adjustment factors. Both of these approaches are empirical and depend on appropriate engineering judgment being made regarding numerous key issues including subsurface variability, soil type and density, strain rate, surface roughness and state of stress among others.

A number of factors are known to affect, in varying degrees, the soil-geomaterial interface behavior. See Table 1 below.

TABLE 1

| Factors Affecting Soil-Geomaterial Interfaces | | |
|---|---|---|
| Type | Factor | Significance |
| Soil | Angularity | High |
| | Density | High |
| | Initial Soil Structure | Low |
| | Mean Grain Size ($D_{50}$) | Medium |
| | Surface Roughness | Low |
| | Uniformity Coefficient ($C_u$) | Low |
| Geomaterial | Surface Hardness | High |
| | Surface Roughness | High |
| Testing | Normal Stress | High |
| | Test Method | Low |
| | Strain Rate | High |

Factors that generally have a lesser effect on the strength of such interfaces include the test method and the soil properties, including initial soil structure and coefficient of uniformity. Other factors, including the normal load, strain rate, particle angularity, mean particle size ($D_{50}$), and the geomaterial hardness and surface roughness may have a significant effect on both the peak and residual interface strength. In particular, the surface roughness and the hardness factors are known to be influential on the interface strength.

Surface roughness, in particular, has been identified as having a significant impact on interface strength. The interface strength increases with surface roughness to a limiting value until it becomes equal to the internal strength of the soil, at which stage shearing is transferred from the interface into the soil. Automated profiling devices are now able to readily quantify the surface characteristics, which has led to the proposal of a large number of international surface roughness standards. The most universally accepted parameter for quantifying surface topography is the average roughness, $R_a$, defined as:

$$R_a = \frac{1}{L}\int_0^L |z|dx \quad (1)$$

where L is the sample length and z is the absolute height of the profile from the mean line. Unfortunately, the $R_a$ parameter may not distinguish between a relatively gently undulating surface and those with a more undulating profile. This limitation can result in surfaces that induce different mechanisms during interface shearing having similar $R_a$ values. Not withstanding this limitation, it is noted that the $R_a$ parameter is typically used to describe surface roughness.

Figure 1:
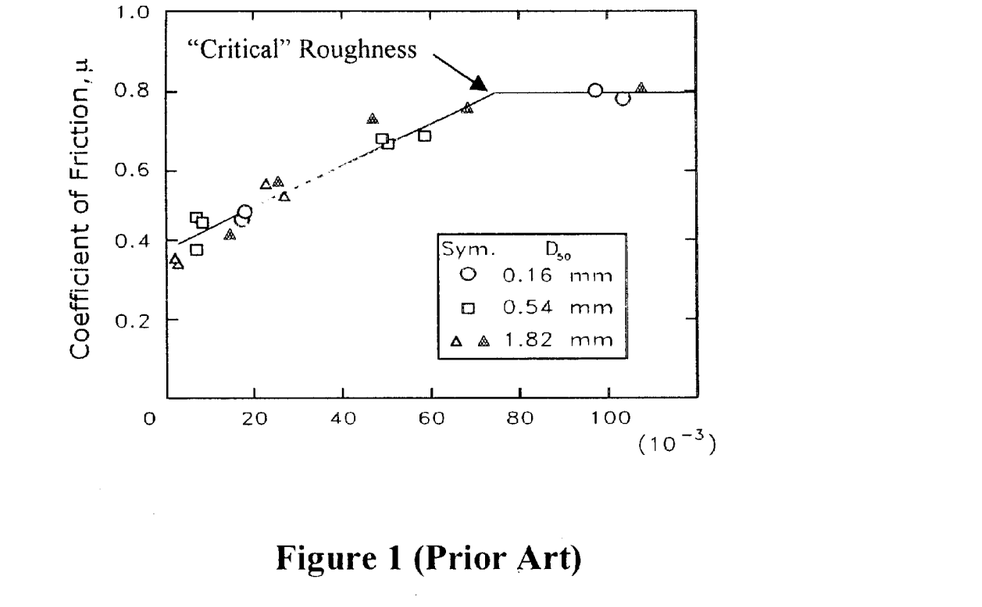
FIG. 1 is a graphical representation of the bilinear relationship between the surface roughness and the frictional coefficient (Prior Art).

Quantification of the role of geomaterial surface roughness on interface strength has necessitated a normalizing of the surface roughness to the average particle size of the contacting soil. The normalized roughness parameter, $R_n$, defined as:

$$R_n = \frac{R_{max}(L = D_{50})}{D_{50}} \quad (2)$$

where $R_{max}$ is the absolute vertical distance between the highest peak and the lowest valley along the surface profile over a sample length equal to $D_{50}$, the average particle diameter. Using $R_n$, the relationship between surface roughness and interface friction was found to be bilinear (see FIG. 1—Prior Art). Along the left-hand portion of the curve, below a certain "critical" roughness, the interface strength increases in a linear fashion proportional to the increase in surface roughness with particles primarily sliding along the surface. At the "critical" surface roughness, shearing transfers from the interface into the adjacent soil body when the interface friction becomes equal to the internal friction angle, or internal frictional strength of the contacting soil, since the normal stress is known. The right-hand portion of the curve reflects an essentially constant coefficient of friction, or internal frictional strength, thus indicating that additional increases in surface roughness above the "critical" surface roughness have no added effect.

Measurement of the particle movements near the interface during interface shear tests is known to show that little particle movement is observed at the interface below peak stresses. Conversely, after peak, the primary mechanism of interface movement is slippage of the soil particles along smooth surfaces, and slipping, rolling, and vertical displacement for rough surfaces while translating along the interface. This behavior is further known to affect an increasing zone of particles as the surface roughness increases. For instance, in smooth surfaces, the particles sliding along the interface dominate the behavior, with minor variations in density being limited to a zone one to two particle diameters thick adjacent to the surface. As the surface roughness increases, the size of the affected zone increases to a distance of about five or six particle diameters from the interface. Thus, the bilinear relationship between the surface roughness and the interface behavior is known to be consistent.

Figure 2:
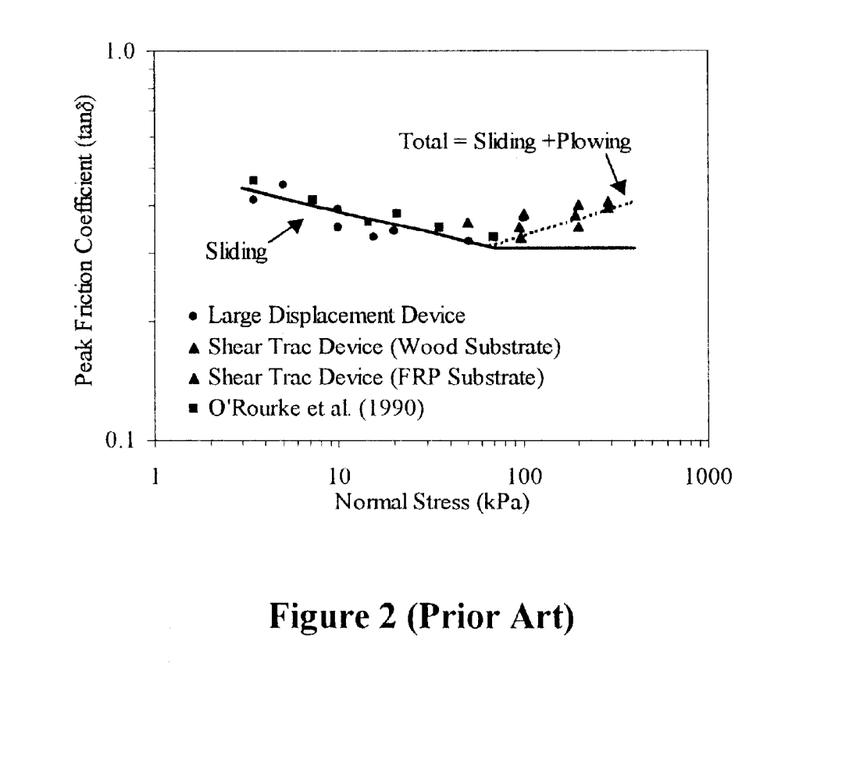
FIG. 2 is a graphical representation of the relationship between particle stress and the frictional coefficient (Prior Art).

The other factor known to have significant impact on the interface behavior is the surface hardness. In tribology, the hardness of the materials present at the interface, in combination with other factors, has been identified to determine the type of surficial wear (e.g. abrasive versus adhesive), the size of the actual contact areas, and the type of contact deformation (e.g. elastic versus plastic) among others. This understanding in tribology has recently been extended to soil-geomaterial interfaces to show that for a given geomaterial hardness, the interface friction will initially decrease as the normal force, and hence, global stress increases. (See FIG. 2—Prior Art). This effect is known to occur because as the normal force increases, the number and area of particles contacting the surface increases, thus causing the actual contact stress per particle to decrease and therefore the interface friction to decrease. At a critical stress, the number and size of individual contacts per unit area reaches a maximum value, causing any additional increase in normal force and hence global stress to be directly transmitted to each particle-surface contact. The mechanism of particle movement at the interface is thus directly related to the magnitude of normal force (or global stress) relative to the hardness of the surface material. At global stresses less than the critical stress, the stress at each particle contact is less than what is required to damage a surface of a given hardness. When this occurs, sliding without damage to the surface is the primary mode of translation. However, when the stresses at particle contacts are greater than the critical stress, particle motion along the surface involves both sliding and plowing.

Plowing occurs when the stresses at the interface exceed what is required to damage the surface, forcing particles to penetrate the surface and remove or displace material from the surface during translation. When plowing occurs in addition to sliding, the force required to displace the soil relative to the surface increases, resulting in an increase in interface friction. The critical stress is dependent on the particulate angularity with the critical stress increasing with decreasing angularity. Furthermore, wearing is more evident at low hardness, while high hardness discourages abrasive wear and changes in surface roughness.

With increasing frequency, the CPT is the device of choice used to obtain in situ measurements of interface strength. The three primary measurements of the CPT are $q_c$, $u_2$ and $f_s$. Factors that have been considered to effect $q_c$ measurements include temperature, the apex angle of the penetrating tip, the wear of the penetrating tip, the penetration rate, and the pore pressure acting on the back of the penetrating tip among others. With the more recent piezocone designs, a portion of the back of the penetrating tip element is exposed, requiring the $q_c$ measurement to be converted to the corrected cone tip resistance, $q_t$, to account for the effect of pore pressure acting on the back of the tip element.

Similarly, the $u_2$ measurement is adversely affected by the degree of saturation of the soil being penetrated and/or that of the porous element, the pore pressure element location, the axial load, and the horizontal stress. For example, incomplete saturation of the porous element may result in a compressible fluid-air mixture that decreases measurement resolution. In addition, the location of the pore pressure element has a significant effect on the measured value. In most soils, the pore pressure rapidly increases at the tip, reaching a maximum value at the shoulder of the CPT, and then decreases until it reaches a stable value. Accordingly, most standard CPT module designs isolate the pore pressure measurement from the $q_c$ measurement, thereby eliminating any interaction.

The friction sleeve measurement $f_s$ involves several factors that affect its measurement accuracy. These factors include load cell arrangement, sleeve surface roughness, sleeve wear, sleeve length, sleeve location and module stiffness.

Load cells are typically arranged in one of two manners—subtraction cone load cell arrangement, where $f_s$ is determined by calculating the difference between the tip and total (sleeve plus tip) load, or isolated load cell arrangement, where the tip and sleeve resistances are measured separately. Of these two designs, the subtraction type load cell arrangements are more common than individual load cell arrangements due to their greater durability and ease of design and manufacturing. However, individual load cell designs can lead to significantly improved resolution of the $f_s$ measurement since $f_s$ is typically more than one order of magnitude less than $q_c$ and, thus, a load cell with a smaller range can be used for the $f_s$ measurements. Since the resolution is a function of the full-scale capacity, a load cell with a smaller range has a higher absolute resolution. ASTM D5778 (1995) estimates that the standard deviation of the $f_s$ measurement for subtraction type designs and individual load cell designs to be 15% and 5% of the full-scale load cell output, respectively. The importance of the CPT load cell arrangement has long been recognized and isolated load cell arrangements are now being incorporated into new penetrometer designs.

ASTM D3441 (1994) and ISSMFE (1989) standards for CPTs specify that the friction sleeve roughness, $R_a$ (average roughness), must be equal to 0.50±0.25 μm. In application, surface roughness measurements may vary greatly, from the time of shipment by the manufacturer, and throughout the service life of the sleeve. The surface roughness may change irregularly with each sounding, decreasing or increasing depending on the soil type encountered and indicative of continuous sleeve wear. Large variations in surface roughness measurements are undesirable, particularly given that a small change in surface roughness can have a large impact on the interface strength of relatively smooth surfaces.

After repeated use, the cone tip and friction sleeve experience significant wear, decreasing in tip and sleeve diameters, respectfully. Usually, the diameter of the sleeve decreases inconsistently along its length, with the top portion wearing more. This uneven wear results in improper contact between the friction sleeve and the soil and may cause as much as a 50% decrease in the $f_s$ measurement. Recognizing the effect of wear, guidelines have also been put forth relative to the control of the effect of CPT tip and friction sleeve wear through national (ASTM D5778 1995) and international (ISSMFE 1989) standards. These standards specify that the friction sleeve diameter should always be equal to or up to 0.35 mm larger in diameter than the cone tip. Prompt replacement of the worn components can maintain the error due to wear below about 5%.

The effect of sleeve length on the $f_s$ measurement is also known to be important. Specifically, the sleeve length adversely affects soil classification, layer detection, and anomaly detection to varying degrees, depending on the statistical properties (i.e. mean, variance, fluctuation distance) of the stratigraphy in a given sounding.

Many researchers have shown that the position of the friction sleeve relative to the CPT tip significantly affects the friction sleeve measurement. Variation in $f_s$ is thought to be primarily due to the variation in horizontal stress acting along a CPT—the "baseline" horizontal stress equal to the natural in situ lateral stress prior to penetration and the variation from the "baseline" stress due to insertion of the CPT. This apparent variation in horizontal stress primarily occurs in a rapidly changing stress zone beginning around the CPT tip and extending up a portion of the CPT shaft. Consequently, $f_s$ measurements outside of the highly variable stress zone are preferable and may be accomplished by positioning the friction sleeve further up the CPT shaft instead of directly behind the CPT tip. Unfortunately, most current designs position the friction sleeve directly behind the tip in accordance with national standards (ASTM D5778 1995).

The module stiffness, of a standard CPT as opposed to a stiff CPT, is known to adversely affect the $f_s$ measurement. "Bending" of the CPT may introduce additional irregularity into the conventional friction sleeve measurement due to "shadowing" of a portion of the sleeve by the tip. While this effect can be minimized by using a full eight gage bridge transducer and increasing the device stiffness to minimize bending, not all penetrometers incorporate these design considerations.

Variations in any of the foregoing factors can significantly affect the measurements obtained during in situ penetration testing and lead to inaccurate data.

Figure 3:
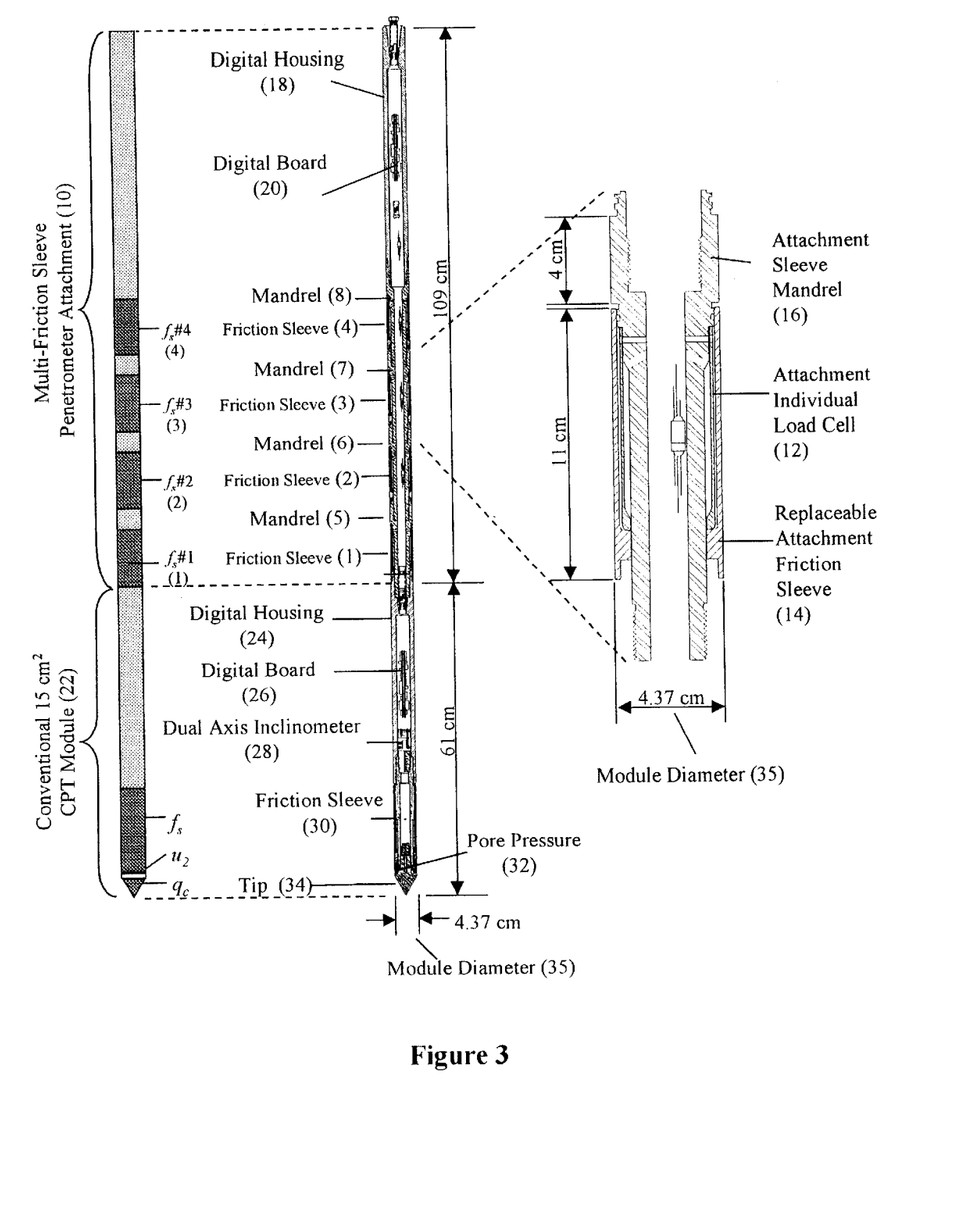
FIG. 3 is a schematic diagram showing the multi-friction sleeve attachment module configured with a conventional CPT module.

As shown in FIG. 3, in a preferred embodiment the multi-friction sleeve penetrometer attachment module (attachment module) 10 is equipped with four individual load cells 12 (i.e. combination of friction sleeve 14 and sleeve mandrel 16) in series, each of which measures the interface resistance due to the penetration of a sleeve 14 with a selected surface texture into the soil. The friction sleeves are vertically arranged in ascending order according to increasing roughness of surface texture. In this manner, the friction sleeve with the least rough surface texture is placed closest to the end of the attachment module that will be coupled to a penetrating tip member, while the friction sleeve with the roughest surface texture is placed at the end of the attachment module that will be furthest away from the penetrating tip member. This configuration provides four individual in situ measurements of interface strength at each measurement depth (i.e. the depths which correspond to the location of each of the friction sleeves) in a single sounding. The load cells 12, digital housing 18 and digital board 20 comprise the attachment module 10, which, in a preferred embodiment, may be attached to a conventional CPT module 22. With the sleeves 14 being interchangeable, sleeves 14 of any desired roughness can be used in a given sounding. In addition, with multiple $f_s$ values being recorded at any given elevation within the same sounding, factors that affect $f_s$ can easily be determined since lateral variability at the site is not an issue. Furthermore, configuration with a conventional CPT module 22 permits simultaneous measurements of conventional CPT sensors (e.g. $q_c$, $f_s$, and $u_2$) in addition to the multi-sleeve attachment measurements. Typically, a CPT module 22 comprises a digital housing 24, a digital board 26, a dual axis inclinometer 28, a friction sleeve 30, a pore pressure tip 32, and a cone tip 34. When used with the CPT 22, the total instrument length is approximately 170 cm, with the attachment module 10 being approximately 109 cm in length including the digital housing 18, and the conventional CPT module 22 being approximately 61 cm in length. (See Table 2 below). It should be noted, however, that non-instrumented tips of varying lengths may be used with the attachment module 10 in place of the conventional CPT module 22.

TABLE 2

Summary of Specifications for a Preferred Embodiment of the Multi-Friction Sleeve Penetrometer.

| | Multi-Friction Sleeve Penetrometer | 15 cm² CPT Module |
|---|---|---|
| Total Length | 109 cm | 61 cm |
| Baseline diameter | 43.7 mm | 43.7 mm |
| Tip Resistance ($q_c$) | N/A | |
| Capacity | | 225 kN |
| Overload Capacity | | 150% |
| Accuracy | | 0.2% |
| Pore Pressure ($u_2$) | N/A | |
| Capacity | | 3.5 Mpa |
| Overload Capacity | | 150% |
| Accuracy | | 0.1% |
| Friction Sleeve ($f_s$) | | |
| Capacity | 45 kN | 45 kN |
| Load Cell | Full Bridge | Full Bridge |
| Overload Capacity | 150% | 150% |
| Precision | 44–89 N | 44–89 N |
| Hysterisis | 22 N | 22 N |
| Length | 11.00 cm | 16.39 cm |
| Surface Area | 151 cm² | 225 cm² |
| Surface Roughness ($R_a$) | 0.50–250 µm | 0.50 µm |
| Inclinometers | | |
| Range | | 20° |
| Accuracy | | 10% |

As seen in FIG. 3 and Table 2, individual, full bridge load cell sensors 12 were selected. Although, subtraction type load cells may be used, with a subtraction design, the fourth sleeve 4 friction would have been determined by subtracting the force acting on the lead module (being either an uninstrumented tip or a CPT module 22 (shown)), the first three attachment sleeves (1, 2, 3), and the exposed mandrel (5, 6, 7) between each consecutive sleeve. The load cell 12 consists of a thin cylinder instrumented on the inside with a full eight strain gauge bridge. The cylinder is separate from the load bearing center mandrel and is loaded in compression by the friction sleeve transferring the sleeve friction to the end of the cylinder. The individual load cell 12 capacities are 45 kN each with an overload tolerance of 150%. The load cells 12 are 11 cm in length, have 150 cm² surface area, and a surface roughness of 0.50–250 µm.

Figure 4:
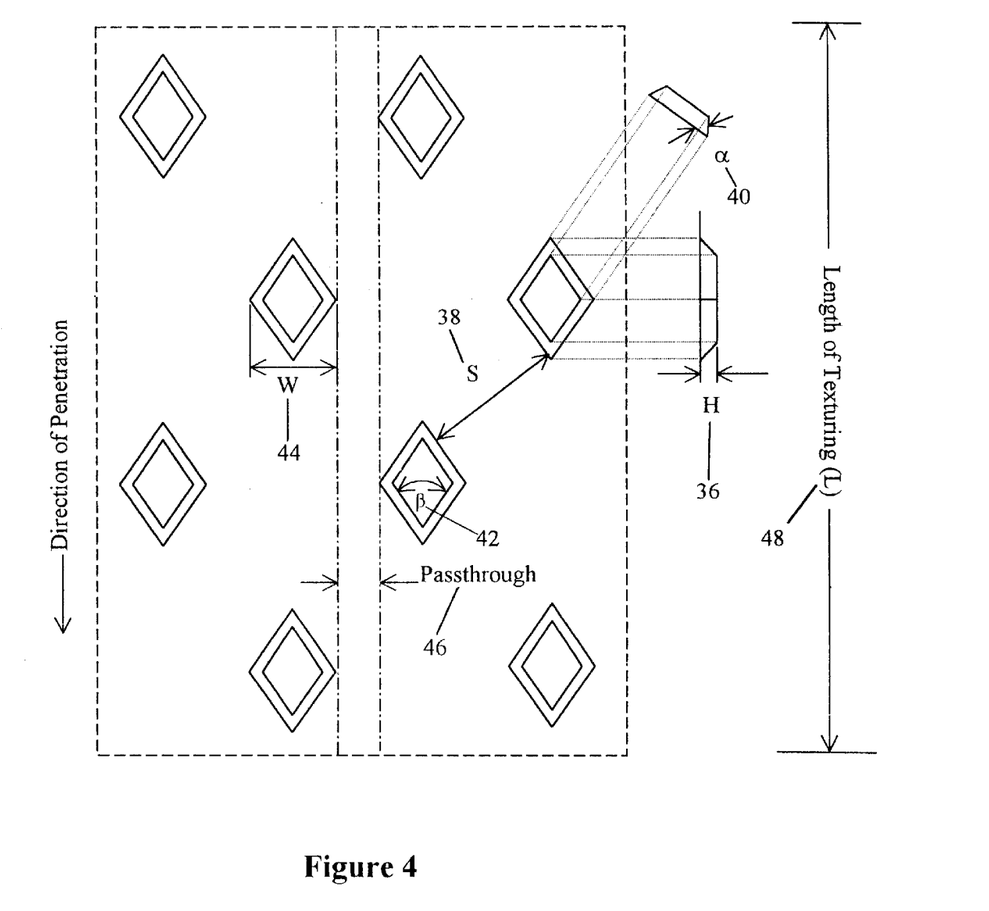
FIG. 4 is a schematic diagram showing a planar projection of a diamond textured sleeve design.

The individual friction sleeves 1–4 can be configured to be removable for ease of assembly and maintenance. The texture of the sleeves 1–4 is designed to be "self-cleaning" and thereby not result in soil particles clogging the texture and changing the surface roughness during a sounding. At the same time, the texture of the sleeves 1–4 is designed to induce internal shearing of the soil, rather than only sliding of soil particles along the interface at high roughness. The percentage passthrough 46 for the textured sleeves 1–4 ranges from 0 to 46 percent. Furthermore, the surface designs are machineable into a wide range of surface roughness values ($R_a$=0.01–116 µm) for conventional geomaterials. Accordingly, the texturing patterns for the attachment module 10 are based on a staggered diamond configuration as shown in FIG. 4, with the corresponding surface roughness values for a number of different roughness parameters shown in Table 3 below. As evident, the average surface roughness ($R_a$) values for the diamond textured sleeves ranged from 0.05 to 250 µm, including the conventional smooth sleeve. Different staggered diamond patterns for the friction sleeves are achieved by varying aspects such as the height (H) 36 between approximately 0.0005 to 2.0 mm, the diagonal spacing (S) 38 between approximately 4.6 to 35.4 mm, and the penetration angle (β) 42 between approximately 5 to 120 degrees. The width (W) 44 and angle (α) 40 remained constant at 5.3 mm and 45 degrees respectively, and the percent passthrough ranges from approximately 0–77%. Each sleeve 1–4 is machined so that the base diameter equals the diameter of a conventional smooth sleeve (44.09±0.05 mm) and so that the diamond pattern extends beyond that surface.

TABLE 3

Summary of Diamond Texturing Pattern Dimensions.

| Diamond Dimension | Range Investigated | Reference Configuration |
|---|---|---|
| Height (H) | 0.0005–20 mm | 1.0 mm |
| Penetration Angle (β) | 15°–120° | 60° |
| Diagonal Spacing (S) | 4.6–12.5 mm | 6.3 mm |
| [Percent Passthrough] | [0–46%] | [16%] |
| Diamond Width (W) | 5.3 mm | 5.3 mm |
| Diamond Angle (α) | 45° | 45° |
| Average Roughness ($R_a$) | 0.5–250 µm | 185 µm |

Figure 5A:
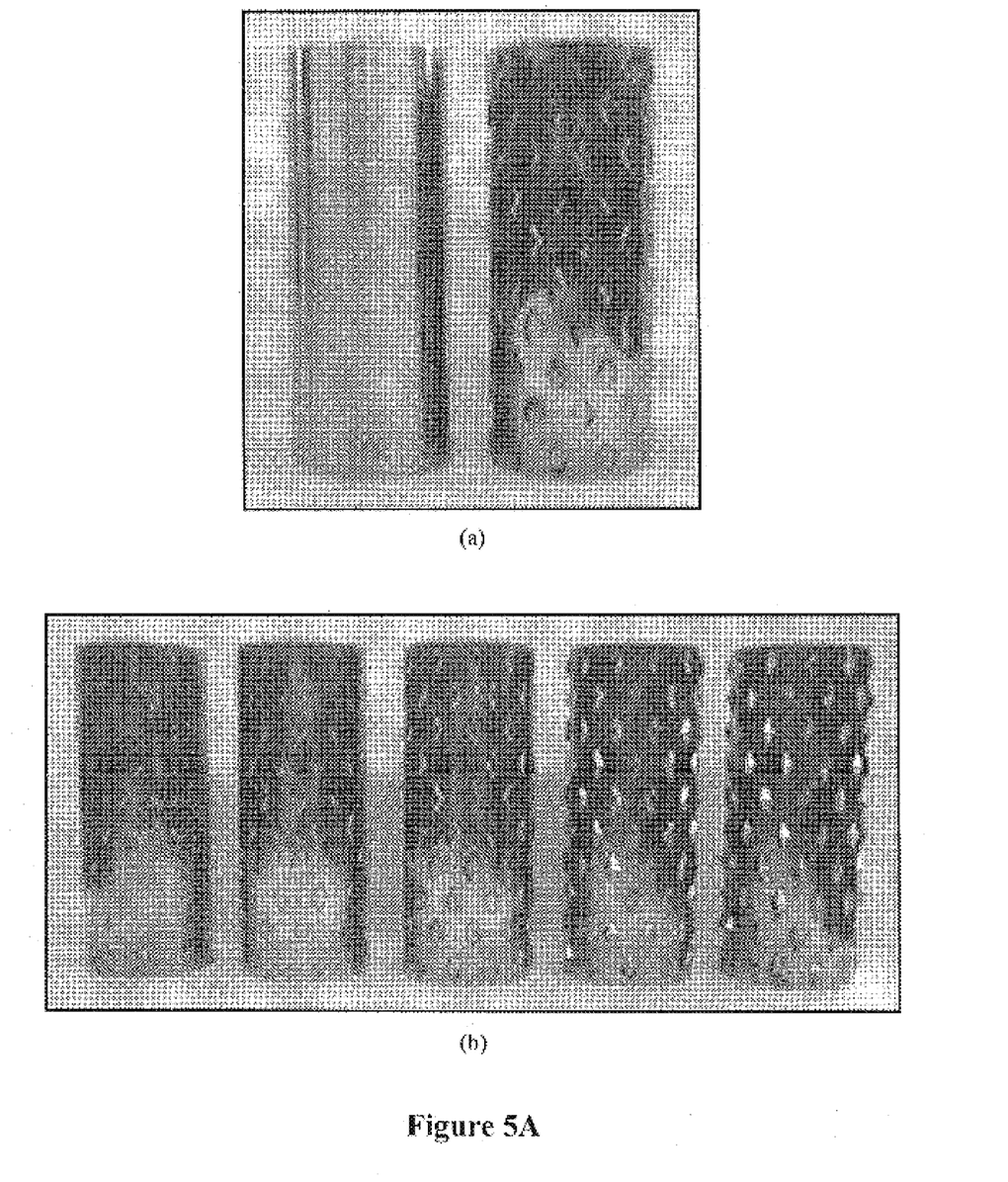
FIGS. 5A and 5B are pictorial representations of sleeves, showing (a) smooth and diamond textured sleeves, (b) increasing roughness, (c) decreasing spacing and (d) increasing penetration angle.
Figure 5B:
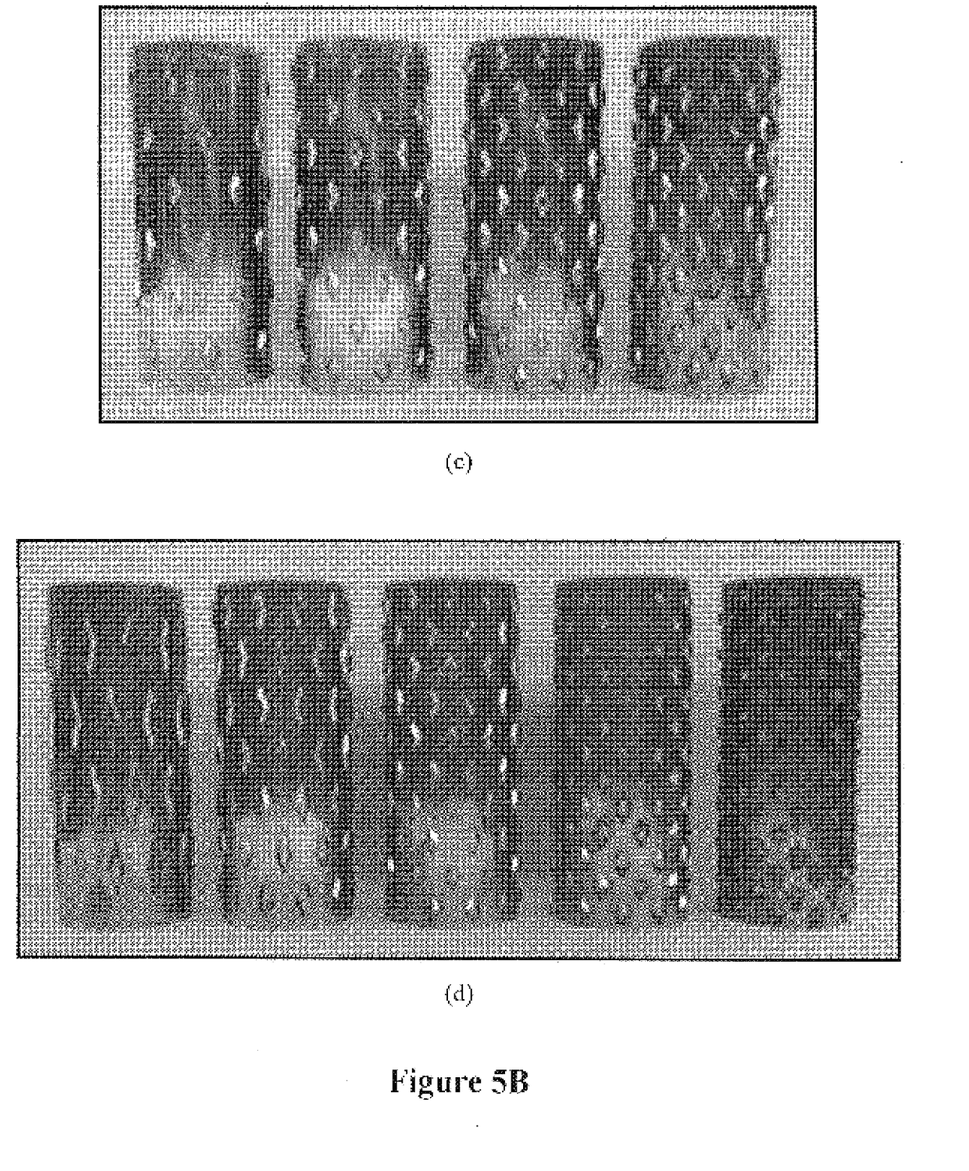

In excess of twenty different diamond surface textured friction sleeves in addition to the conventional smooth sleeve have been manufactured and tested for application with the attachment module. The textured sleeves were specifically designed to investigate the effect of diamond height (H) 36, diagonal spacing (S) 38, penetration angle (β) 42, and length of texturing (L) 48 on the friction sleeve measurement. FIGS. 5A and 5B show friction sleeves, including (a) illustrating a conventional smooth sleeve and a diamond surface textured sleeve; (b) showing sleeves of increasing roughness; (c) showing sleeves of decreasing spacing 38; and (d) showing sleeves with increasing penetration angle 42.

Due to the bilinear relationship of surface roughness to interface strength, small changes in roughness have a negligible effect on the interface strength so long as surface roughness is in the stable upper portion of the curve (see FIG. 1). In the present embodiment having diamond patterned sleeves 1–4, the pattern design is relatively resistant to wear since the individual asperities, or diamonds, have a large projected cross-sectional area. Nonetheless, it is recommended that all sleeves be machined out of a prehardened metal alloy with a Rockwell C hardness of about 30. Such hardness, as was used for the diamond patterned sleeves, will minimize wear and extend the service life while maintaining relative ease in machining. Accordingly, it is anticipated that minor changes due to wear in surface roughness on most diamond textured sleeves should have a negligible effect on the measured sleeve friction.

Since it is evident that a shorter sleeve 1–4 provides increased sensitivity to soil classification and stratigraphic features, including distinct interfaces and thin soil layers, the present embodiment utilizes a sleeve having a shorter length of only 11 cm, as opposed to a more typical length of 16.39 cm. In addition, the sleeves 1–4 are positioned well behind the penetrometer tip, thus negating the requirement that the CPT sleeve length 30 be about 3 to 5 times the module diameter 35 (ASTM D5778 1995) (see FIG. 3). As the sleeve friction was found to vary near the tip as a result of the highly sheared zone that developed around the tip during penetration, a standard sleeve length to diameter ratio was established in an attempt to normalize this effect between different size penetrometers (i.e. 10 and 15 cm²). In a preferred embodiment, the sleeves 1–4 are 11 cm long (surface area=151 cm²), which results in a surface area similar to the standard 10 cm² sleeve (150 cm²). The minimum length of the attachment sleeves 1–4 is determined by the need to ensure that an adequate surface area, necessary for the effect of the texture to be established, is possible and that a practical perspective, as far as dimensional constraints of the individual load cell system, is selected.

As shown in FIG. 3, the module attachment 10 is designed for ready assembly behind a conventional CPT module 22. In this configuration, conventional CPT $q_c$, $f_s$, and $u_2$ measurements are obtained in the same sounding and provide the opportunity to compare the module attachment 10 measurements with the standardized in situ measurements. This configuration enables rapid identification of the subsurface stratigraphy encountered in each sounding and separates the differences due to lateral variability from those due to changes in sleeve texture.

Since one objective of the multi-friction sleeve attachment module 10 is to obtain multiple measurements of interface strength under the same conditions and in the same sounding, all attachment sleeves 1–4 are optimally positioned beyond the influence of the high shear zone. To meet these requirements, a conventional 15 cm² CPT module 22 with an extended electronic housing 24, 26 enabled the lead edge of the first (lowest) attachment sleeve 1, $f_s$#1, to be located 61 cm (~14 diameters) behind the CPT tip 34. In embodiments where an uninstrumented tip may be used instead of a CPT tip 34, the positioning of the sleeves 1–4 beyond the influence of the high shear zone around the tip is still recommended.

The attachment module 10 is designed to permit efficient disassembly/reassembly between soundings and further permits modifications with only minimal adjustments. As shown in FIG. 3, the attachment module 10 is a jointed mandrel design whereby each individual load cell unit (mandrel 5–8, load cell 12, and sleeve 1–4) is comprised of separate components. With this modularity, the number of different custom components is minimized. Furthermore, modifications to individual load cells 12 can be performed with relative ease and a damaged load cell unit 12 can be easily replaced with a backup unit in the field. In addition, the number of individual load cells 12 can be increased or decreased freely since each load cell unit 12 is mechanically self contained and the data acquisition system 68 (see FIG. 6) can be configured for a range of different configurations with only minor adjustments.

In order to counteract any adverse affects on the measurement of the friction sleeves 1–4 behind the tip 34 due to inadequate module stiffness, the connections between the attachment module 10 and the CPT module 22 are of sufficient stiffness. In particular, the connections between the CPT 22 and attachment 10, and between each structural component of the attachment 10 are designed to withstand estimated lateral forces that could induce module bending under common testing configurations. The module stiffness between the CPT 22 and the attachment 10 is additionally increased by minimizing the inner diameter of the sleeve mandrels 16. This minimization is facilitated by the size of the cable required for down-hole digital processing is smaller than the cable required for conventional up-hole signal conditioning.

The attachment module is further configured for use below the water table and, therefore, a watertight seal should be maintained in the areas where electronics are present. The watertight seal is accomplished by sealing each joint with one or more O or X-rings.

Figure 6:
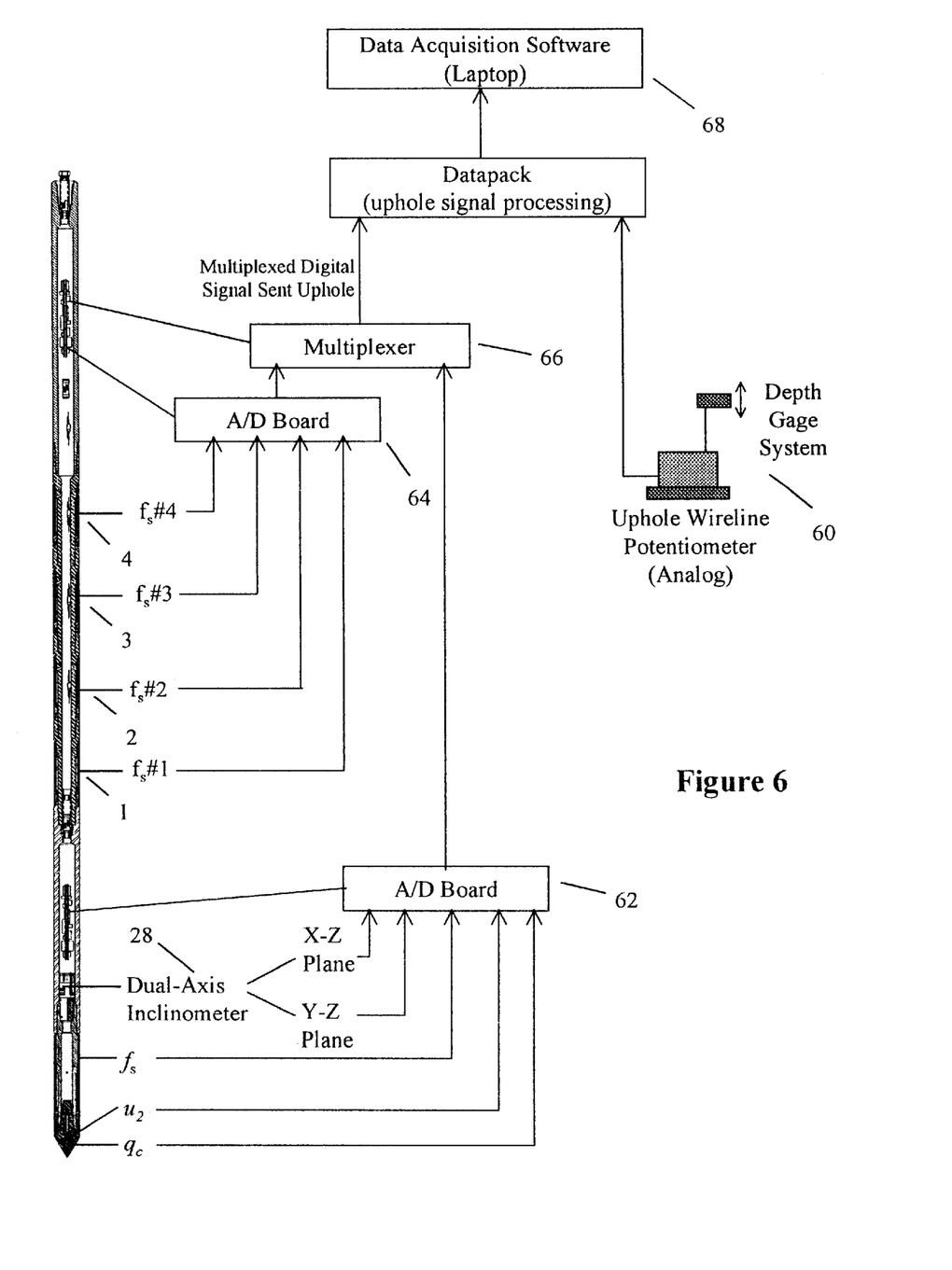
FIG. 6 is a schematic diagram of the data acquisition system for the combined CPT module-attachment module system.

The attachment module 10 is further configured with a data acquisition system that allows real-time review of data. FIG. 6 is a schematic of the data acquisition system used in conjunction with the attachment module 10 and with a conventional CPT 22. The hardware in the CPT module 22 is used to measure the $q_c$, $f_s$, and $u_2$ values and the hardware in the attachment module 10 is used to individually measure the force on each of the four sleeves 1–4 ($f_s$#1, $f_s$#2, $f_s$#3, and $f_s$#4) at each measurement increment. In addition, a dual axis inclinometer system 28 is incorporated in the CPT module 22 to enable continuous monitoring of verticality during penetration. Penetration depth is monitored up-hole using a wireline potentiometer 60. With nine individual measurements being obtained downhole by the complete CPT module 22 and attachment module 10 system, a downhole analog-to-digital signal conditioning system 62 is used. To maintain the independence of the CPT module 22, the CPT analog signals are conditioned and converted to digital signals separately within the CPT module 22 housing. The attachment module 10 signals are conditioned in a similar fashion in a A/D board 64 and then multiplexed 66 with the digital signals from the CPT module 22 and relayed up-hole to the data acquisition system 68.

When in use, a series of calibration tests should be performed to assess the performance of the multi-friction sleeve attachment system. First, prior to assembly of the attachment module 10, each load cell 12 should be individually calibrated, without signal conditioning against a NIST traceable load cell, by applying an excitation directly to the full bridge and monitoring the output during a load-unload cycle. Second, each attachment module 10 load cell 12 in the fully assembled CPT-attachment module should be calibrated by undergoing a load-unload cycle against a NIST traceable load cell. This calibration enables both the calibration of each load cell 12 through the signal conditioning system, as well as assessment of mechanical cross-talk between the multiple sleeve load cells.

In another embodiment, a method is provided for obtaining multiple sleeve friction measurements at each measurement depth within a single sounding and enhances the data obtained in conventional CPT soundings with measurements of sleeve friction for different sleeve surface roughnesses. In particular, the attachment module 10 system provides a method for obtaining seven simultaneous measurements at each measurement increment while monitoring module verticality, full analog-to-digital conversion and multiplexing of signals downhole, the arrangement of four individual sleeve load cell sensors in series, and the ability to rapidly exchange sleeves 1-4 between consecutive soundings. The diamond texturing pattern for sleeves is "self-cleaning" and, depending on the dimensions of the diamonds, induces shearing within the soil as opposed to at the interface, thus providing more accurate frictional measurements. The individual, modular load cell 12 design performs well and has a linear calibration range with minimal hysteresis and mechanical cross-talk between individual sleeve load cells 12.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. An apparatus for determining interface strength in situ at a particular subsurface location, said apparatus comprising:
- a penetrating tip member, said penetrating tip member configured to penetrate into soil of said subsurface location; and
- an attachment module coupled to said penetrating tip member, wherein said attachment module includes a plurality of individual electrically isolated load cells, wherein each load cell measures a soil response separately;
- wherein each load cell obtains an in situ measurement of interface strength at each measurement depth that corresponds to the location of each load cell on the attachment module; and
- wherein each load cell obtains the in situ measurement of interface strength without using the measurement data of the penetrating tip member.

2. The apparatus of claim 1, further comprising a data acquisition system coupled to at least one of said penetrating tip member and said attachment module.

3. The apparatus of claim 1, further comprising a data acquisition system, said data acquisition system comprises:
- means for measuring penetration depth of said penetrating tip member and said attachment module;
- means for measuring penetrating tip member measurement values;
- means for measuring verticality of said penetrating tip member;
- means for measuring frictional forces at each measurement increment on each of a plurality of friction sleeves located in the corresponding plurality of individual electrically isolated load cells; and
- wherein said data acquisition system enables contemporaneous review of frictional data.

4. The apparatus of claim 3, wherein the measurement data from each of said means for measuring is converted to digital signals, multiplexed, and then relayed to the data acquisition system.

5. The apparatus of claim 1, wherein the attachment module further comprises a hollow inner chamber for containing data and power components.

6. The apparatus of claim 5, wherein frictional measurements from attachment module are transmitted to a data acquisition system.

7. The apparatus of claim 1, wherein the penetrating tip member further comprises a conventional CPT module.

8. The apparatus of claim 1, wherein each of the plurality of said load cells is comprised of a mandrel and a friction sleeve.

9. The apparatus of claim 8, wherein each of said friction sleeves is configured with a surface texture, where said surface texture has a corresponding surface roughness value;
- each of said surface textures for select friction sleeves is configured to induce internal shearing of the soil as the attachment module is penetrated into the soil; and
- each of said surface textures is further configured to be self-cleaning, such that soil particles do not clog the texture and change the surface roughness value during a sounding.

10. The apparatus of claim 9, wherein each of said friction sleeves has a corresponding value at a measurement depth in a single sounding, and said values correspond to individual in situ measurements of interface strength at said measurement depth.

11. An apparatus for determining interface strength in situ at a particular subsurface location, comprising:
- a penetrating tip member, said penetrating tip member configured to penetrate into soil of said subsurface location;
- an attachment module coupled to said penetrating tip member, wherein said attachment module includes a plurality of individual load cells;
- a data acquisition system coupled to at least one of said penetrating tip member and said attachment module;
- wherein said penetrating tip member further comprises a conventional CPT module instrumented to measure $q_c$, $u_2$, and $f_s$, and having a CPT digital housing, CPT digital board, dual axis inclinometer and CPT friction sleeve;
- wherein each of the plurality of said load cells is comprised of a mandrel and a friction sleeve; said each of said friction sleeves is configured with a surface texture, where said surface texture has a corresponding surface roughness value;
- each of said surface textures for select friction sleeves is configured to induce internal shearing of the soil as the attachment module is penetrated into the soil; and
- each of said surface textures is further configured to be self-cleaning, such that soil particles do not clog the texture and change the surface roughness value during a sounding; and
- a vertical arrangement of said friction sleeves in ascending order according to increasing roughness of said surface texture, such that the least rough friction sleeve is placed closest to the penetrating tip member and the roughest friction sleeve is placed furthest away from said penetrating tip member.

12. The apparatus of claim 11, wherein the friction sleeves are spaced from the penetrating tip member such the friction sleeves are located outside of a high shear zone occurring around the penetrating tip member.

13. The apparatus of claim 12, wherein the friction sleeves have an average surface roughness of approximately 0.05 to approximately 250 um.

14. The apparatus of claim 13, wherein each of said friction sleeves is further configured with a diamond surface texture; and
- said diamond surface texture having geometric parameters, including diamond height, diagonal diamond spacing, penetration angle, and diamond width, that are variable to impart different characteristics to the textured surfaces of said friction sleeves.

15. The apparatus of claim 14, wherein said geometric parameters of each of the diamond surface textures is further configured by diamond height variations from approximately 0.25 to approximately 2.0 mm, diagonal spacing from approximately 4.6 to approximately 12.5 mm, and penetration angles from approximately 30 to approximately 120 degrees.

16. A method of determining interface strength in situ comprising the steps of:
- positioning a penetrating tip member so as to penetrate into soil at a particular subsurface area;
- positioning an attachment module in a predetermined relationship to the penetrating tip member so as to form a penetrometer comprised of at least said penetrating tip member and said attachment module;
- forcing the penetrating tip member end of the penetrometer into the soil;

collecting penetrating tip member measurements; and collecting attachment module measurements from a plurality of individual electrically isolated load cells, wherein each of the load cells measures the soil response separately;

wherein each load cells obtains an in situ measurement of interface strength at each measurement depth that corresponds to the location of each load cell on the attachment module;

wherein each load cell obtains the in situ measurement of interface strength without using the measurement data of the penetrating tip member.

17. The method of claim 16, further comprising transmitting said data corresponding to said penetrating tip member measurements and said attachment module measurements to a data acquisition system.

18. The method of claim 16, wherein the penetrating tip member is a conventional CPT module.

19. The method of claim 16, wherein each of said load cells of said attachment module is comprised of a corresponding plurality of mandrels and friction sleeves; and further comprising a method for measuring the interface resistance for each of said friction sleeves, where said interface resistance data is used to determine corresponding interface strength.

20. The method of claim 16, further including the steps of:

measuring penetration depth of said penetrometer;

measuring penetration tip member values; and measuring verticality of said penetrating tip member;

where the penetration depth, penetration tip member values, and verticality measurements comprise the drive tip measurements; and measuring frictional forces at each measurement increment on each of a plurality of friction sleeves located in the corresponding plurality of individual load cells, where the frictional force data comprises the attachment module measurements.

21. The method of claim 20, further comprising the steps of converting the analog measurement data from each of said measurements to digital signals, multiplexing, and then relaying the multiplexed data to the data acquisition system.

22. A method of determining interface strength in situ comprising the steps of:

positioning a penetrating tip member so as to penetrate into soil at a particular subsurface area;

positioning an attachment module in a predetermined relationship to the penetrating tip member so as to form a penetrometer comprised of at least said penetrating tip member and said attachment module;

forcing the penetrating tip member end of the penetrometer into the soil;

collecting penetrating tip member measurements;

collecting attachment module measurements from a plurality of load cells, each of said load cells of said attachment module is comprised of a corresponding plurality of mandrels and friction sleeves, said plurality of friction sleeves are configured to be removable, such that the arrangement of the friction sleeves along the attachment module portion of the penetrometer may be reconfigured into different order arrangements for measuring corresponding interface resistances of said friction sleeves;

transmitting said data corresponding to said penetrating tip member measurements and said attachment module measurements to a data acquisition system; and measuring the interface resistance for each of said friction sleeves, where said interface resistance data is used to determine corresponding interface strength.

23. The method of claim 22, wherein said friction sleeves are spaced from the penetrating tip member such that the friction sleeves are located outside of a high shear zone occurring around the penetrating tip.

24. The method of claim 22, wherein the friction sleeves are configured with a surface texture; and said surface texture of select friction sleeves is configured with a diamond-shaped pattern so as to induce internal shearing of the soil around the penetrometer as the penetrometer is penetrated into the soil.

25. The method of claim 24, wherein the friction sleeves are arranged in ascending order of vertically according to increasing roughness of the surface texture, such that the least rough friction sleeve is placed closest to the penetrating tip member and the roughest friction sleeve is placed furthest away from said penetrating tip member.

26. An apparatus for determining interface strength in situ at a particular subsurface location, comprising:

a penetrating tip member configured to penetrate into soil of said subsurface location; and an attachment module coupled to said penetrating tip member, wherein said attachment module includes a plurality of load cells, wherein each load cell includes a friction sleeve, said friction sleeve of at least one load cell being configured with a different surface texture than another load cell.

27. The apparatus of claim 26, wherein the penetrating tip member further comprises a conventional CPT module.

28. The apparatus of claim 26, further comprising a data acquisition system coupled to at least one of said penetrating tip member and said attachment module.

29. The apparatus of claim 28, wherein frictional measurements from the attachment module are transmitted to said data acquisition system.

* * * * *